United States Patent
Power

(10) Patent No.: US 7,062,957 B2
(45) Date of Patent: Jun. 20, 2006

(54) PERCOLATION TEST APPARATUS

(75) Inventor: Martin Power, Fethard-On-Sea (IE)

(73) Assignee: Arcaid International Limitged, Wexford (IE)

(*) Notice: Subject to any disclaimer, the term of this patent is extended or adjusted under 35 U.S.C. 154(b) by 0 days.

(21) Appl. No.: 10/499,084

(22) PCT Filed: Dec. 17, 2002

(86) PCT No.: PCT/IE02/00172

§ 371 (c)(1),
(2), (4) Date: Jun. 15, 2004

(87) PCT Pub. No.: WO03/054307

PCT Pub. Date: Jul. 3, 2003

(65) Prior Publication Data

US 2005/0103101 A1   May 19, 2005

(30) Foreign Application Priority Data

Dec. 20, 2001   (IE) .............................. S2001/1097

(51) Int. Cl.
*E21B 47/00*   (2006.01)
*E21B 47/12*   (2006.01)

(52) U.S. Cl. ........................ 73/152.06; 73/38
(58) Field of Classification Search ............. 73/152.06, 73/38, 73, 861.24
See application file for complete search history.

(56) References Cited

U.S. PATENT DOCUMENTS 3,892,126 A * 7/1975 Curtin ........................ 73/38
3,926,143 A * 12/1975 Hothan ....................... 116/228
3,945,247 A * 3/1976 Anderson ..................... 73/73
4,072,044 A * 2/1978 Farwell et al. ................ 73/38
4,099,406 A * 7/1978 Fulkerson ..................... 73/73
4,182,157 A * 1/1980 Fink .......................... 73/38
4,341,110 A * 7/1982 Block ........................ 73/38
4,561,290 A * 12/1985 Jewell ........................ 73/38
4,627,118 A * 12/1986 Baker ........................ 4/510
4,829,817 A * 5/1989 Kozlowski ................ 73/152.41
4,867,874 A * 9/1989 Aubert et al. ............... 210/169
5,601,236 A * 2/1997 Wold ......................... 239/63
6,050,779 A * 4/2000 Nagao et al. ................ 417/28
6,098,448 A * 8/2000 Lowry et al. ................. 73/38
6,105,418 A * 8/2000 Kring ......................... 73/38
6,251,167 B1 * 6/2001 Berson ....................... 95/263
6,324,922 B1 * 12/2001 Hanks ...................... 73/863.12
6,571,605 B1 * 6/2003 Johnson ...................... 73/38
6,652,893 B1 * 11/2003 Berson ....................... 426/67
6,887,383 B1 * 5/2005 Potts ........................ 210/620
6,938,461 B1 * 9/2005 Johnson ...................... 73/38
2004/0195177 A1 * 10/2004 Potts ........................ 210/620

* cited by examiner

Primary Examiner—Charles Garber
Assistant Examiner—Rodney Frank
(74) Attorney, Agent, or Firm—Botkin & Hall, LLP

(57) ABSTRACT

A percolation test apparatus comprises a water tank (12), a pipe (36) for directing water from the tank into a hole (20) in the ground, an on-off valve (32) for controlling the flow of water in the conduit, and a water level sensor (30) for detecting the level of water in the hole. To perform a test a control unit (14) automatically turns the valve on and off at times determined by the level of water detected by the sensor. To avoid collapse of the hole, and to ensure the correct size of hole for the test, a cage (16) is lowered into the hole. A rain-proof cover (18) prevents rain from falling onto the cage or the ground surrounding the cage.

20 Claims, 6 Drawing Sheets

PERCOLATION TEST APPARATUS

This invention relates to a percolation test apparatus for establishing the water soakage capacity of the soil.

Government regulations relating to the percolation testing of soil require that holes of certain dimensions are dug into the ground, water poured into the holes at certain intervals and the drop in level of the water measured. Such testing is labor intensive and requires attendance at the test site throughout the test.

It is an object of the invention to provide an apparatus for facilitating such testing.

According to the present invention there is provided a percolation test apparatus comprising a water tank, a conduit for directing water from the tank into a hole in the ground, an on-off valve for controlling the flow of water in the conduit, a water level sensor means for detecting the level of water in the hole, and control means for automatically turning the valve on and off at times determined at least in part by the level of water detected by the sensor means.

Preferably the apparatus further includes a cage for insertion into the hole, the water from the conduit being directed into the cage. The apparatus may further include a rain-proof cover for the cage, the cover extending substantially beyond the cage on all sides to prevent rain from falling onto the cage or the ground surrounding the cage.

Figure 1:
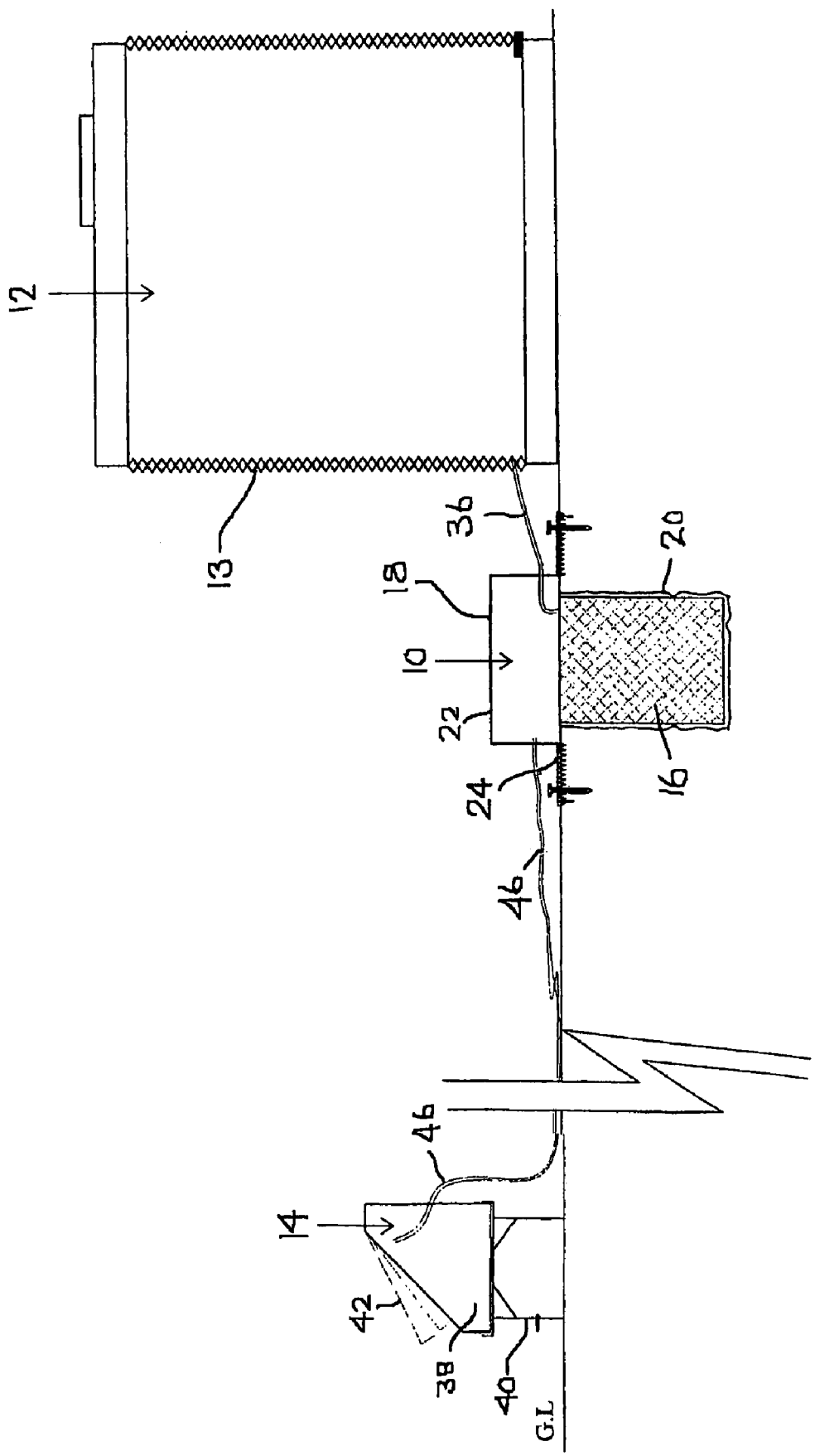
Figure 2:
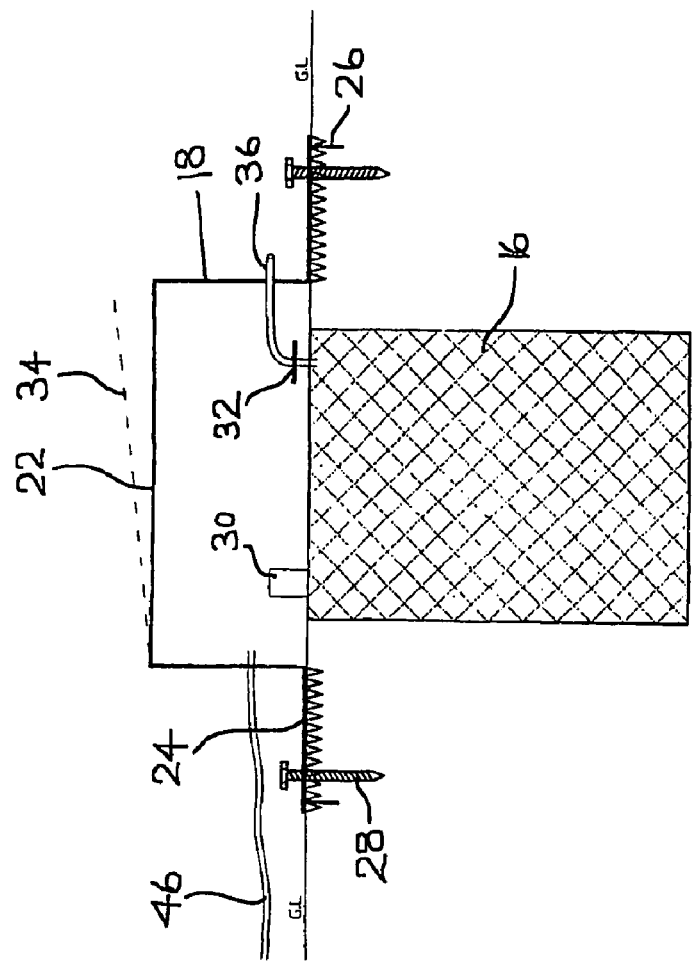
Figure 2:
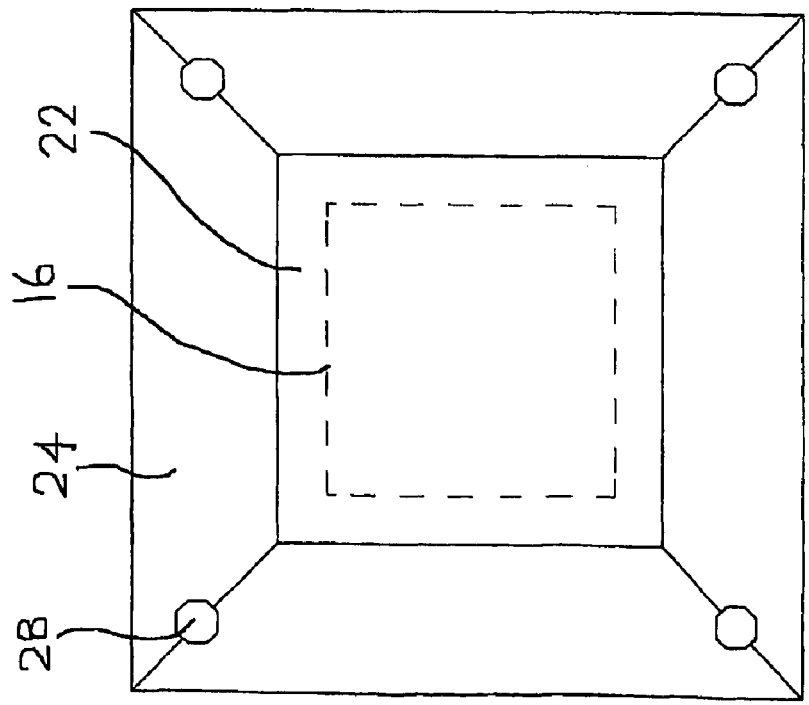
Figure 3:
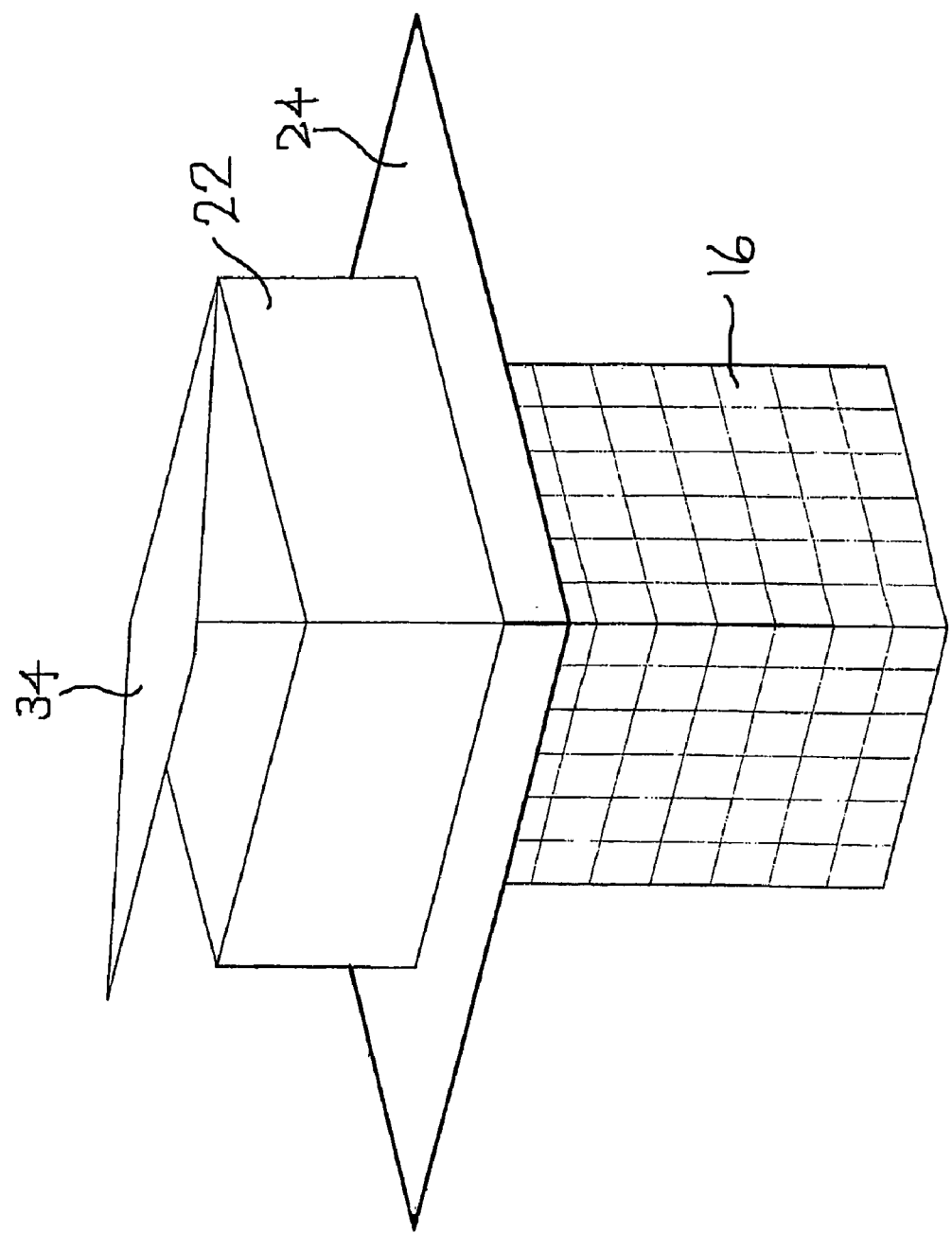
Figure 4:
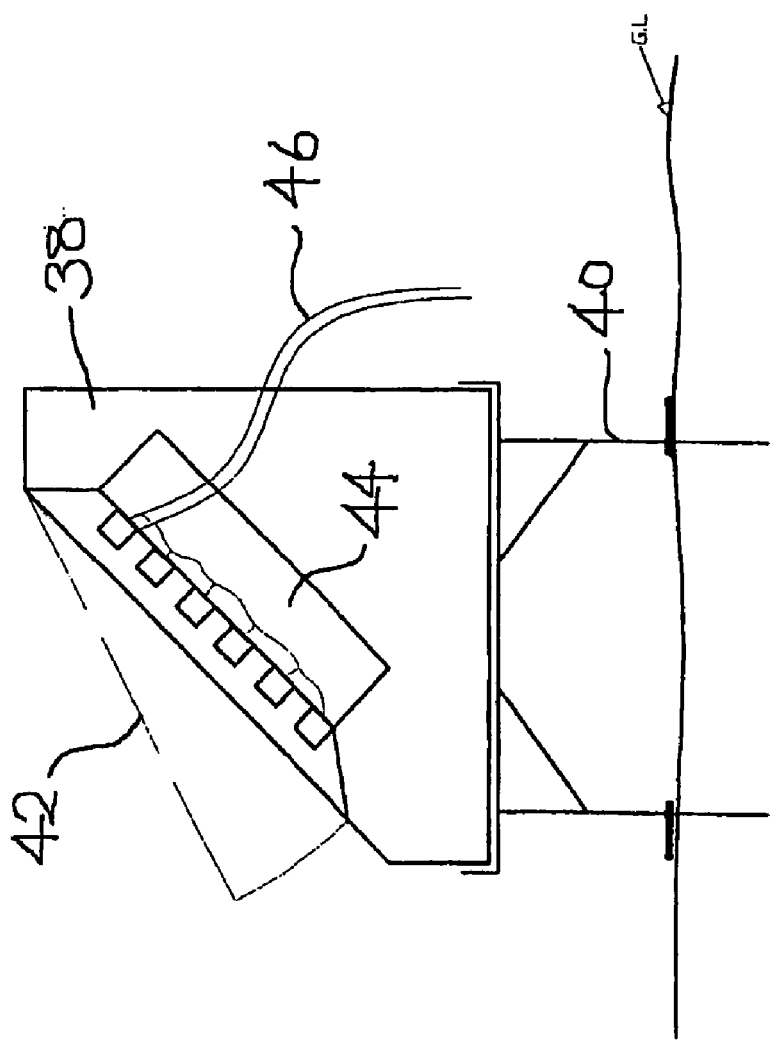
Figure 4:
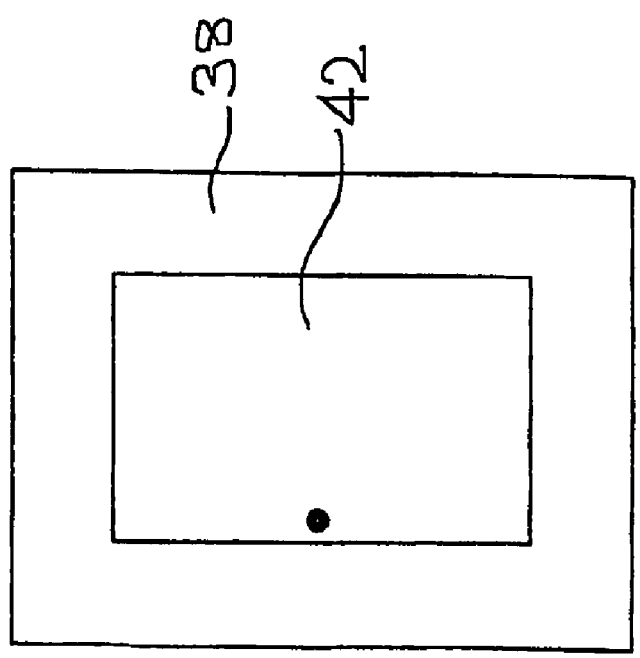
Figure 5:
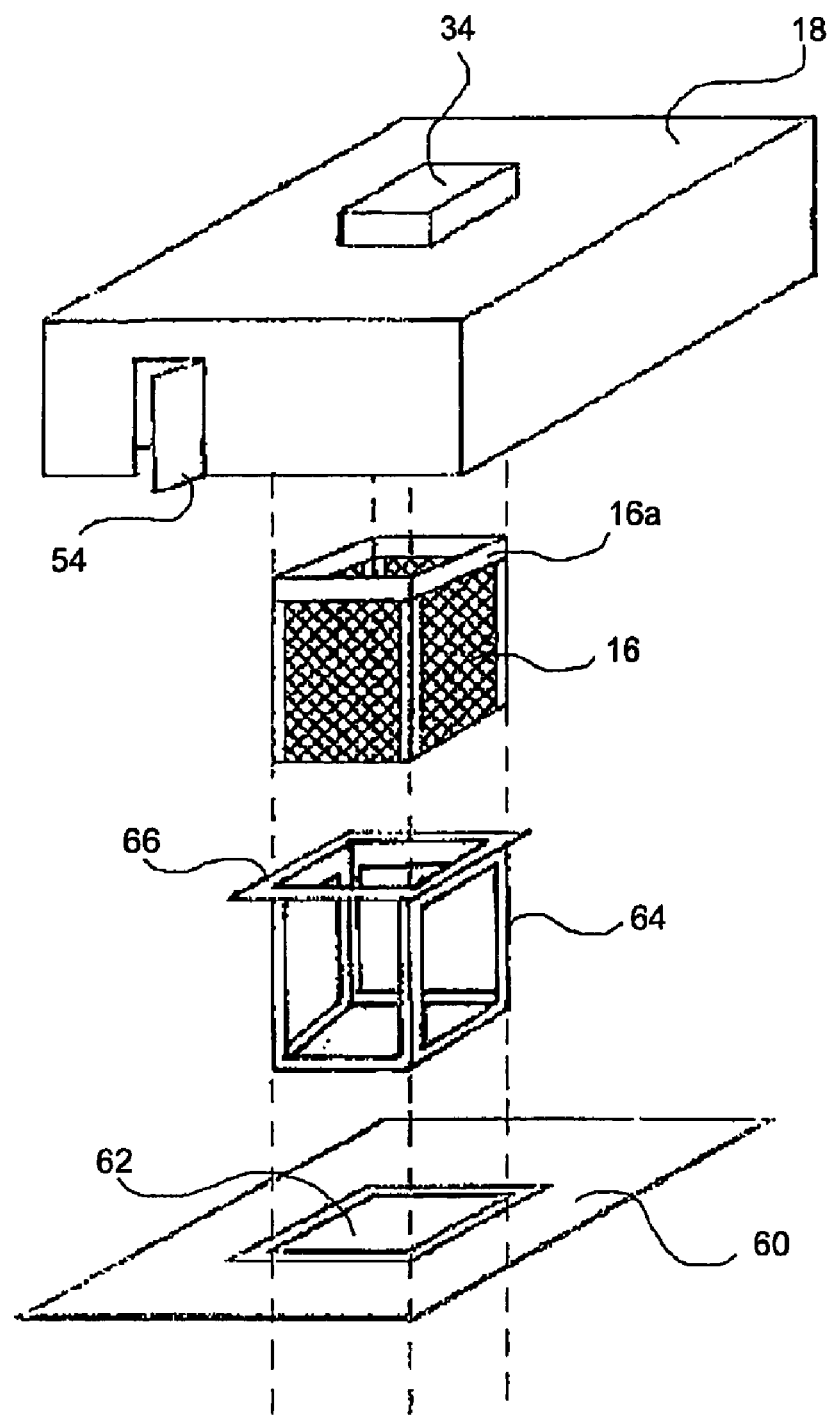
Figure 6:
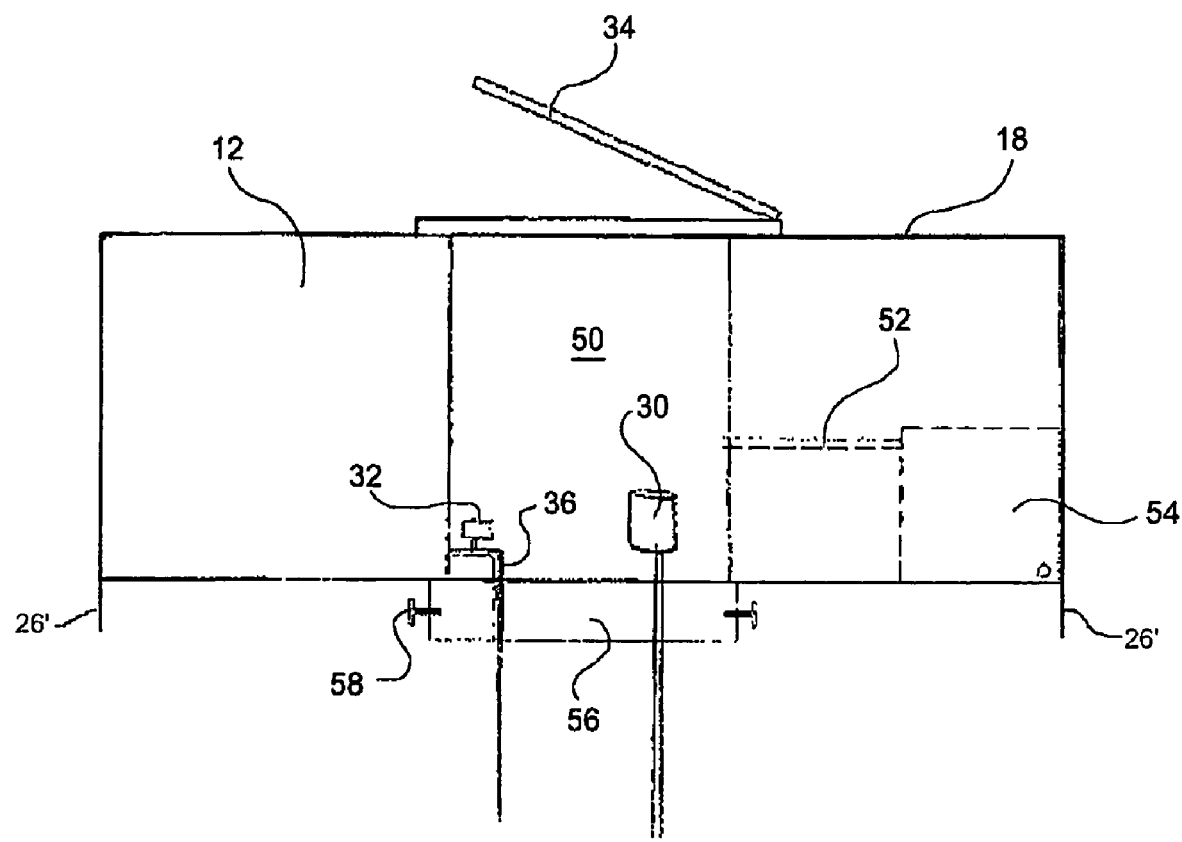

Embodiments of the invention will now be described, by way of example, with reference to the accompanying drawings, in which:

FIG. 1 is a schematic diagram of an apparatus according to the invention;

FIGS. 2(a) and 2(b) are, respectively, plan and sectional side views of the test unit of FIG. 1;

FIG. 3 is a perspective view of the test unit of FIG. 2;

FIGS. 4(a) and 4(b) are, respectively, plan and sectional side views of the control unit of FIG. 1;

FIG. 5 is an exploded view of an alternate form of test unit for use in the apparatus of FIG. 1; and FIG. 6 is a cross-sectional side view of the combined cover/water tank of FIG. 5.

Referring first to FIGS. 1 to 4, a first embodiment of percolation test apparatus comprises three main components, a test unit 10, a water tank 12 and a control station 14. As will be described below, percolation testing normally involves undertaking several tests simultaneously, and in such case a number of test units 10 are used which are controlled by a single control station 14 and may share a common water tank 12. However, the basic set-up is one of each unit.

The test unit 10 comprises a mesh cage 16 and a cover 18 and can be made of one or more of steel, stainless steel, timber, plastic, aluminum, PVC or other corrosion-resistant material. The cage 16 has a square or cylindrical horizontal cross-section and in use it is lowered into a test hole 20 dug in the ground so that the top of the cage lies flush with the ground level GL. The cage 16 allows water introduced into the cage to penetrate the face of the test hole 20 and also ensures that the test hole does not collapse during a test, therefore ensuring the integrity of the test. The cage 16 will also act as a tool for ensuring that the size of the test hole 20 is correct according to the regulations applicable to the test being undertaken (various different sized cages can be provided for use in different tests).

The cover 18 is generally "hat"-shaped and comprises a central housing 22 surrounded by a flat peripheral flange 24. The cover 13 sits on the ground with the housing 22 over the cage 16 and the flange 24 extends substantially beyond the cage 16 on all sides. The purpose of the cover 18 is to seal the cage 16 and test hole 20 from any rainwater or surface water penetration, ensuring the integrity of the test by not allowing any uncontrolled water into the test hole. Thus the cover 18 itself prevents rain from falling onto the cage or the ground surrounding the cage, while a sharp rim 26 around the periphery of the flange 24 is driven into the ground to provide a seal which resists the penetration of rainwater laterally under the cover. The cover 18 is secured in position on the ground by pinning the four corners of the flange 24 to the ground using pins 28. The cage 16 may depend from and be supported by the housing 22, or it may be a separate component.

The housing 22 contains an analog water level sensor 30 and a solenoid-operated water valve 32 and, optionally, other instruments or systems required to operate a test. The water level sensor 30 may be of any suitable type. The cover 18 is weather proof and has a hinged, lockable access door 34 for maintenance and operation purposes. The test unit 10 bears a unique code number for the purpose of identification and calibration.

Typical dimensions of the test unit 10 are as follows:
The cover 18: is 700 mm square.
The housing 22: is 400 mm square by 150 mm height.
The cage 16: is 300 mm square.
Depth of cage 16: 400 mm The water tank 12 is preferably made of a strong plastics materials and typically has a capacity to hold 30 gallons (113.56 liters). In use the water tank is located within 1 meter of the test unit 10. A semi-rigid pipe 36 connects the water tank 12 to the test unit 10. The pipe 36 passes through the wall of the housing 22 to deliver water into the top of the cage 16, and hence into the hole 20, via the on-off valve 32. The walls 13 of the water tank 12 are preferably of "concertina" construction so that it can be stored in a collapsed state. The water tank 12 will therefore inflate as it is filled with water prior to testing, and collapse as testing progresses and the water content reduces. A colorant can be added to the water to help identify a situation where the test water entered a well or river.

The control station 14 can, like the test unit 10, be made of one or more of steel, stainless steel, timber, plastic, aluminum, PVC or other corrosion-resistant material. It comprises a sealed and weather-proof housing 38 which can be supported on a stand 40, as shown in the drawings, or it can sit on the test unit 10. It has a hinged, lockable access door 42 for maintenance and operations purposes.

The control station 14 contains a computer control system 44 including a power source, CPU, screen, keyboard, analogue input/output cards, digital input/output cards, modem, GPS (Global Positioning System), alarm system and associated wiring. The computer system 44 is connected by a multi-core cable 46 to the test unit 10—in particular, the cable 46 is connected to the sensor 30 and the valve 32 and to any other components in the housing 22. By this means the computer system 44 can sense the instantaneous level of water in the cage 16 and operate the on-off valve 32 to deliver water from the tank 12 into the cage 16 at desired times.

In general the computer system 44 is able to instruct the, or in the case of several test units, each test unit 10 to perform a particular percolation test and record the results as the test proceeds. The particular test to be performed at the, or each, test unit 10 can be programmed into the system 44 by the operator or it may be selected from a menu of pre-programmed tests. In general each test (which may be different at each unit 10) comprises turning the valve 32 on and off at times according to a schedule determined at least in part by the instantaneous level of water in the hole 20 detected by the sensor 30.

The following is one typical test, known as a P1 test, but the use of the apparatus is not limited to this particular test. As stated above, a number of tests may be performed at the same time, using a number of test units controlled by a single control station. However, the following describes just one test at a single test hole.

The set-up process begins when the test unit 10 is placed in the test hole 20 and the water tank 12 is filled and connected to the test unit.

The test process begins by the operator pressing a "Start Test" button. In response thereto the display shows the GPS position, which the operator must confirm. This is recorded in the computer memory to be printed in the summary results. After the GPS position has been confirmed, the computer system 44 starts the test by switching on the solenoid valve 32 to fill water into the test hole. The computer system 44 now controls the following steps:

a. Shut valve 32 when water level reaches 400 mm (i.e. top of test hole)(as read by sensor 30).
b. 7 hours later open valve 32 to fill level to 400 mm again and shut valve.
c. 17 hours later open valve 32 to fill level to 400 mm again and shut valve.
d. Wait for water level to drop to 300 mm.
e. Record time taken for the water level to drop from 300 mm to 200 mm.
f. Open the valve to fill level to 300 mm again and shut valve.
g. Wait for water level to drop to 200 mm.
h. Record time taken for the water level to drop from 300 mm to 200 mm.
i. Open valve 32 to fill level to 300 mm again and shut valve.
j. Wait for water level to drop to 200 mm.
k. Record time taken for the water level to drop from 300 mm to 200 mm.
l. Calculate the P-value for that particular test hole by dividing the total time recorded at steps e, h and k by 3 and then dividing the result by 4.

The result is summarized together with the results of like tests. The summary can be obtained remotely via the modem or locally by, for example, connecting a laptop to the system. The result may also be sent from the site in the form of a text message where the system includes a GSM modem. Also, the computer system 44 could be in communication with a remote computer and could be arranged to transmit results to the remote computer. This remote computer could store the results and generate standard reports in either electronic or paper format to satisfy standard requirements. These reports could also include photos taken at the site and transmitted to the remote computer.

The test criteria i.e. the amount of water to be discharged, the intervals between the discharges and the duration of soakage and its recording are as set out by government agencies from time to time. The above apparatus can be adjusted to take account of new test criteria as issued by the government agencies.

FIGS. 5 and 6 show an alternate form of test unit 10 which may be used in the apparatus of FIG. 1 in place of the test unit shown in FIGS. 1 to 4. In FIGS. 5 and 6, the same reference numerals have been used for components which are the same or equivalent to those of FIGS. 1 to 4.

In the alternate test unit, the rain-proof cover 18 incorporates the water tank 12 to form a single rigid unit. In this case the water tank 12 is a generally rectangular annulus defining a central opening 50. A flange 26' depends from around the periphery of the tank 12 to act as a seal to prevent water entering the test hole when the test unit is in position. The pipe 36 is tapped into the inside wall of the tank and leads down into the hole 20 in use. The central opening 50 houses the sensor 30 and valve 32 and is closed by a lockable access door 34. Control wires (not shown) connected to the sensor 30 and valve 32 extend through a conduit 52 running through the tank to terminate in a socket (not shown) in the exterior wall of the tank. The socket is exposed by opening a door 54. The cable 46 (FIGS. 1 and 2) is provided with a complementary plug for inserting in the socket.

A skirt 56 depends from the periphery of the central opening 50 and, in use, the upper end 16a of the cage 16 is retained in the skirt by thumb screws 58 so that the cage 16 depends from the cover/tank 18. The unit also includes a rectangular baseplate 60 having a rectangular central opening 62, and an open frame 64.

In use, the hole 20 is dug and the plate 60 placed on the ground with the opening 62 centered over the hole. Next the frame 64 is lowered into the hole 20 through the opening 62 until a flange 66 around the upper edge of the frame comes to rest on the plate 60 around the edge of the opening 62. Finally, the cover/tank 18 with dependent cage 16 affixed thereto is lowered towards the plate 60 so that the cage 16 is slidably received into the frame 64, the frame 64 being just slightly dimensionally larger than the cage 16. Thus the frame 64, pre-located in the ground as described, serves as a guide for the subsequent insertion of the cage 16.

The invention is not limited to the embodiments described herein which may be modified or varied without departing from the scope of the invention.

The invention claimed is:

1. A percolation test apparatus comprising a water tank, a conduit for directing water from the tank into a hole in the ground, an on-off valve for controlling the flow of water in the conduit, a water level sensor means for detecting a variable level of water in the hole, and a programmable computer-based control means responsive to the sensor means for automatically turning the valve on and off according to selected test criteria programmed into the control means at times determined at least in part by the instantaneous level of water in the hole and for recording the time taken for the water level to drop from one pre-determined level to another.

2. An apparatus as claimed in claim 1, further including a cage for insertion into the hole, the water from the conduit being directed into the cage.

3. An apparatus as claimed in claim 2, further including a rain-proof cover for the cage, the cover extending substantially beyond the cage on all sides to prevent rain from falling onto the cage or the ground surrounding the cage.

4. An apparatus as claimed in claim 3, wherein the cover houses the on-off valve and the water level sensor means.

5. An apparatus as claimed in claim 3, wherein the cage depends from and is supported by the cover.

6. An apparatus as claimed in claim 3, wherein the cover has a rim which penetrates the ground to resist the penetration of rainwater under the cover.

7. An apparatus as claimed in claim 1, wherein the water tank is collapsible.

8. An apparatus as claimed in claim 3, wherein the cover comprises the water tank.

9. An apparatus as claimed in claim 8, wherein the water tank has a central opening which houses the on-off valve and the water level sensor means, the cage depending from the periphery of the central opening.

10. An apparatus as claimed in claim 9, further including an open frame for initial location in the hole and adapted to slidably receive the cage lowered into it.

11. An apparatus as claimed in claim 1, wherein the control means is remote from the on-off valve and the water level sensor means.

12. A percolation test apparatus comprising a water tank, a conduit for directing water from the tank into a hole in the ground, an on-off valve for controlling the flow of water in the conduit, a water level sensor means for detecting the level of water in the hole, control means for automatically turning the valve on and off at times determined at least in part by the level of water detected by the sensor means, a cage for insertion into the hole, the water from the conduit being directed into the cage, and a rain-proof cover for the cage, the cover extending substantially beyond the cage on all sides to prevent rain from falling onto the cage or the ground surrounding the cage, the cover including the water tank.

13. An apparatus as claimed in claim 12, wherein the control means further includes means for recording the time taken for the water level to drop from one pre-determined level to another.

14. An apparatus as claimed in claim 12, wherein the cover houses the on-off valve and the water level sensor means.

15. An apparatus as claimed in claim 12, wherein the cage depends from and is supported by the cover.

16. An apparatus as claimed in claim 12, wherein the cover has a rim which penetrates the ground to resist the penetration of rainwater under the cover.

17. An apparatus as claimed in claim 12, wherein the water tank is collapsible.

18. An apparatus as claimed in claim 12, wherein the water tank has a central opening which houses the on-off valve and the water level sensor means, the cage depending from the periphery of the central opening.

19. An apparatus as claimed in claim 18, further including an open frame for initial location in the hole and adapted to slidably receive the cage lowered into it.

20. An apparatus as claimed claim 12, wherein the control means is remote from the on-off valve and the water level sensor means.

* * * * *